United States Patent
Canty et al.

(10) Patent No.: US 7,518,716 B2
(45) Date of Patent: Apr. 14, 2009

(54) GRANULAR PRODUCT INSPECTION DEVICE

(75) Inventors: Thomas M. Canty, Williamsville, NY (US); Paul J. O'Brien, East Aurora, NY (US); Christian P. Marks, Cheektowaga, NY (US); Richard E. Owen, Youngstown, NY (US)

(73) Assignee: J.M. Canty Inc., Buffalo, NY (US)

( * ) Notice: Subject to any disclaimer, the term of this patent is extended or adjusted under 35 U.S.C. 154(b) by 805 days.

(21) Appl. No.: 10/740,244

(22) Filed: Dec. 18, 2003

(65) Prior Publication Data

US 2004/0184649 A1    Sep. 23, 2004

Related U.S. Application Data

(60) Provisional application No. 60/435,528, filed on Dec. 20, 2002.

(51) Int. Cl.
*G01N 21/00* (2006.01)
*G06K 9/00* (2006.01)
*B07C 5/342* (2006.01)

(52) U.S. Cl. .................... 356/237.1; 382/141; 382/110; 209/576; 209/580

(58) Field of Classification Search ... 356/237.1–237.3, 356/600–622; 382/110, 156, 227, 141; 209/511, 209/576, 580, 588, 578, 581, 582, 638, 639; 73/865.5, 865.8
See application file for complete search history.

(56) References Cited

U.S. PATENT DOCUMENTS 4,338,024 A    7/1982    Bolz et al. .................... 356/23

4,540,286 A *  9/1985    Satake et al. ................. 356/445
4,830,194 A    5/1989    Kajiura et al. ............... 209/580

(Continued)

FOREIGN PATENT DOCUMENTS

DE    10125277    9/2002

(Continued)

OTHER PUBLICATIONS

PartAn Laboratory Analyzer, http://www.sci-tec-inc.com/plaboratory.html, pp. 1-2, Sci-Tec Inc., Dec. 15, 2003.

(Continued)

*Primary Examiner*—Sang Nguyen
(74) *Attorney, Agent, or Firm*—Darby & Darby

(57) ABSTRACT

An inspection device for inspecting a granular product includes a feed tray having a receiving region for receiving the granular product and an imaging region and a vibration device configured to impart vibrations to the feed tray for moving granules of the granular product from the receiving region to the imaging region. The inspection device also includes an image capturing device configured to capture an image of a sample of the granular product in an image area of the imaging region. In addition, a method for inspecting a granular product includes disposing the granular product on a receiving region of a feed tray, vibrating the feed tray so as to induce a movement of the granular product from the receiving region of the feed tray to an imaging region of the feed tray, and capturing an image of a sample of the granular product in an image area of the imaging region.

29 Claims, 5 Drawing Sheets

U.S. PATENT DOCUMENTS

| | | | | |
|---|---|---|---|---|
| 4,976,540 | A | 12/1990 | Kitamura et al. | 356/38 |
| 4,993,838 | A | 2/1991 | Tresouthick et al. | 356/439 |
| 5,074,158 | A * | 12/1991 | Tokoyama | 73/865.8 |
| 5,129,268 | A * | 7/1992 | Uesugi et al. | 73/865.5 |
| 5,135,114 | A | 8/1992 | Satake et al. | 209/558 |
| 5,239,358 | A | 8/1993 | Tokoyama | 356/244 |
| 5,261,285 | A | 11/1993 | Tokoyama | 73/864.81 |
| 5,309,773 | A | 5/1994 | Tokoyama | 73/863.01 |
| 5,321,496 | A | 6/1994 | Shofner et al. | 356/238 |
| 5,396,333 | A | 3/1995 | Aleshin et al. | 356/385 |
| 5,733,592 | A | 3/1998 | Wettstein et al. | 426/416 |
| 5,917,927 | A * | 6/1999 | Satake et al. | 382/110 |
| 5,956,413 | A * | 9/1999 | Oste et al. | 382/110 |
| 6,427,128 | B1 | 7/2002 | Satake et al. | 702/81 |
| 2002/0127586 | A1 | 9/2002 | Mortensen | 435/6 |
| 2004/0151360 | A1 * | 8/2004 | Pirard et al. | 382/141 |

FOREIGN PATENT DOCUMENTS

| | | |
|---|---|---|
| EP | 1213051 | 6/2002 |
| EP | 1273901 | 1/2003 |
| GB | 2249829 | 5/1992 |
| JP | 2001212525 A * | 8/2001 |

OTHER PUBLICATIONS

PartAn—Video Image Analysis, http://www.sci-tec-inc.com/image.html, pp. 1-3, Sci-Tec Inc., Dec. 15, 2003.

Pellet-Scan-System PS-25C (Colour Camera), http://www.ocsgmbh.com/data/products/ps-25c.php, pp. 1-2, Dec. 15, 2003.

* cited by examiner

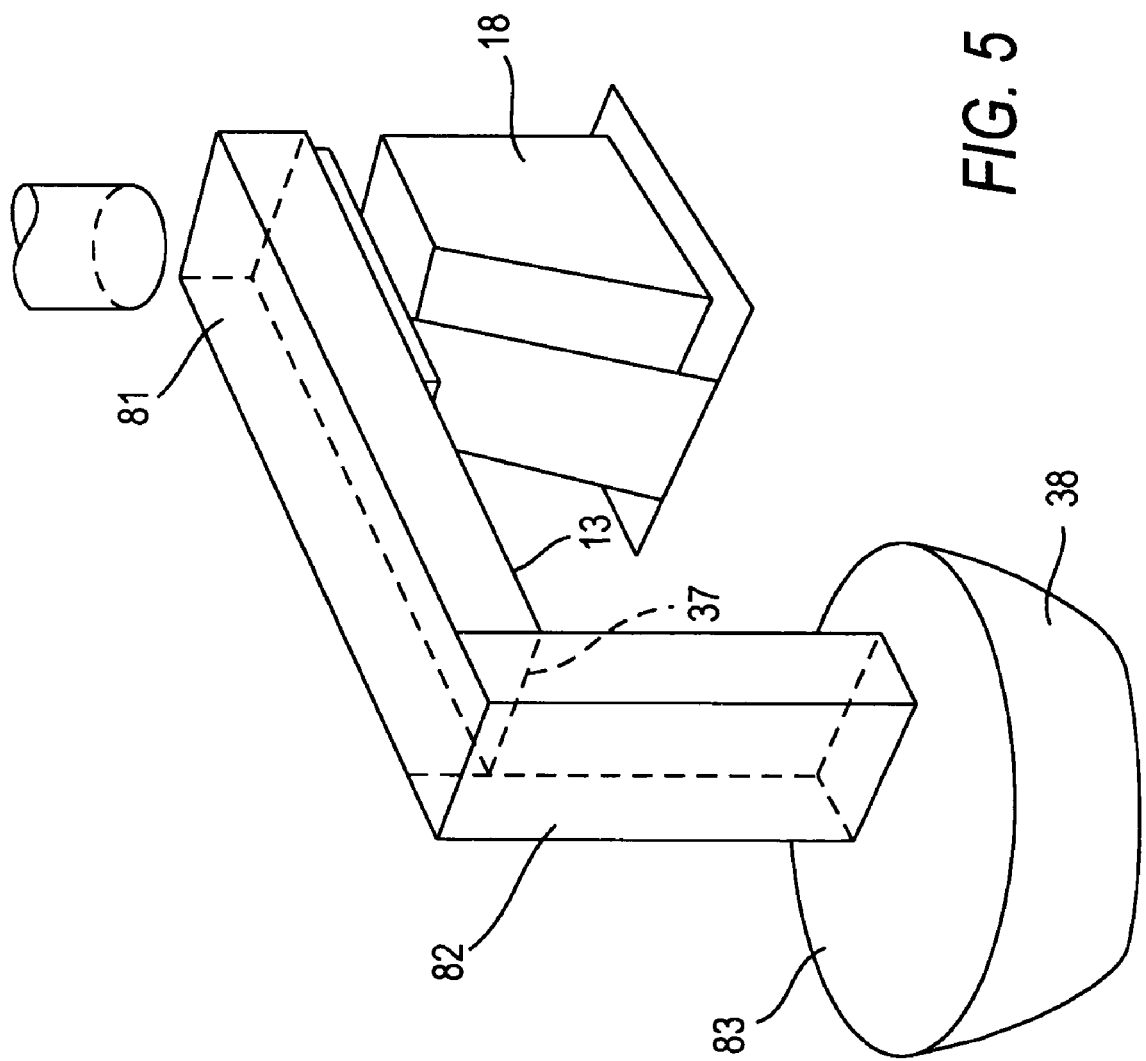

GRANULAR PRODUCT INSPECTION DEVICE

BACKGROUND OF THE INVENTION

The present invention relates generally to an inspection device and method, and more particularly to a device and method for inspecting a granular product.

In the production granular products including powders, there is a desire to inspect the product to determine various qualities of the product, such as size, shape and color characteristics of the granules and the presence and quantity of any impurities, as well as characteristics of those impurities. Other qualities that may be desired to be determined include flow characteristics of the granules and granule surface characteristics.

Granular products include powders as well as coarser mixtures of granules. Examples of granular products that may be inspected include pharmaceutical products, food products (rice, grain, cereals, flour, confections, sugar, etc.), cosmetic products, aggregates, ores, plastics and other petrochemical products, and many more.

Various methods and devices for performing such an analysis have been employed for these purposes which may employ laser diffraction, spectroscopy, and various forms of visual image analysis.

A problem in inspecting granular products, particularly when image analysis is employed, is in presenting the product to the image capturing device so as obtain an optimal image of the product. It is desired, for example, to have a controllable quantity of the product within the image area so that an image can be made of the desired quantity. In addition, it is desired to have a controlled and uniform spread of the material so that the image represents a fair sampling of the product. It is also desirable to be able to control a thickness of the spread of material in the image area, depending on what type of characteristics are being determined. In some cases a single layer of granules is required to achieve imaging of substantially all of the product, for example, if it is necessary to show the complete absence of a particular defect. In other cases, it may be desired to have less than a single layer, i.e., with space between the individual granules for improved inspection of individual granule characteristics. In still other cases, a thicker layer of granules may be desired when a sampling of the product characteristics is sufficient. It is also desired to present the granules to an image capturing device in an even manner, so that the granules being imaged are on a single plane and/or at a given distance from the imaging device.

BRIEF SUMMARY OF THE INVENTION

An object of the present invention is to provide an inspection device and method for inspecting a granular product that is capable of presenting a quantity of the granular product in an image area in a controlled manner.

An alternate or additional object of the present invention is to provide a device for presenting a sample of the granular product to an image area having a controlled thickness that may include a single layer of particles or multiple layers of particles. A further alternate or additional object is to provide a device that enables specific inspection conditions to be easily repeatable for subsequent inspections.

The present invention provides an inspection device for inspecting a granular product that includes a feed tray having a receiving region for receiving the granular product and an imaging region and a vibration device configured to impart vibrations to the feed tray for moving granules of the granular product from the receiving region to the imaging region. The inspection device also includes an image capturing device configured to capture an image of a sample of the granular product in an image area of the imaging region.

The present invention also provides a method for inspecting a granular product that includes disposing the granular product on a receiving region of a feed tray, vibrating the feed tray so as to induce a movement of the granular product from the receiving region of the feed tray to an imaging region of the feed tray, and capturing an image of a sample of the granular product in an image area of the imaging region.

BRIEF DESCRIPTION OF THE DRAWINGS

Several embodiments of the present invention are elaborated upon below with reference to the accompanying drawings, in which:

FIG. 5 shows a partial schematic representation of an inspection device having a cover for the feed tray.

DETAILED DESCRIPTION

Figure 1:
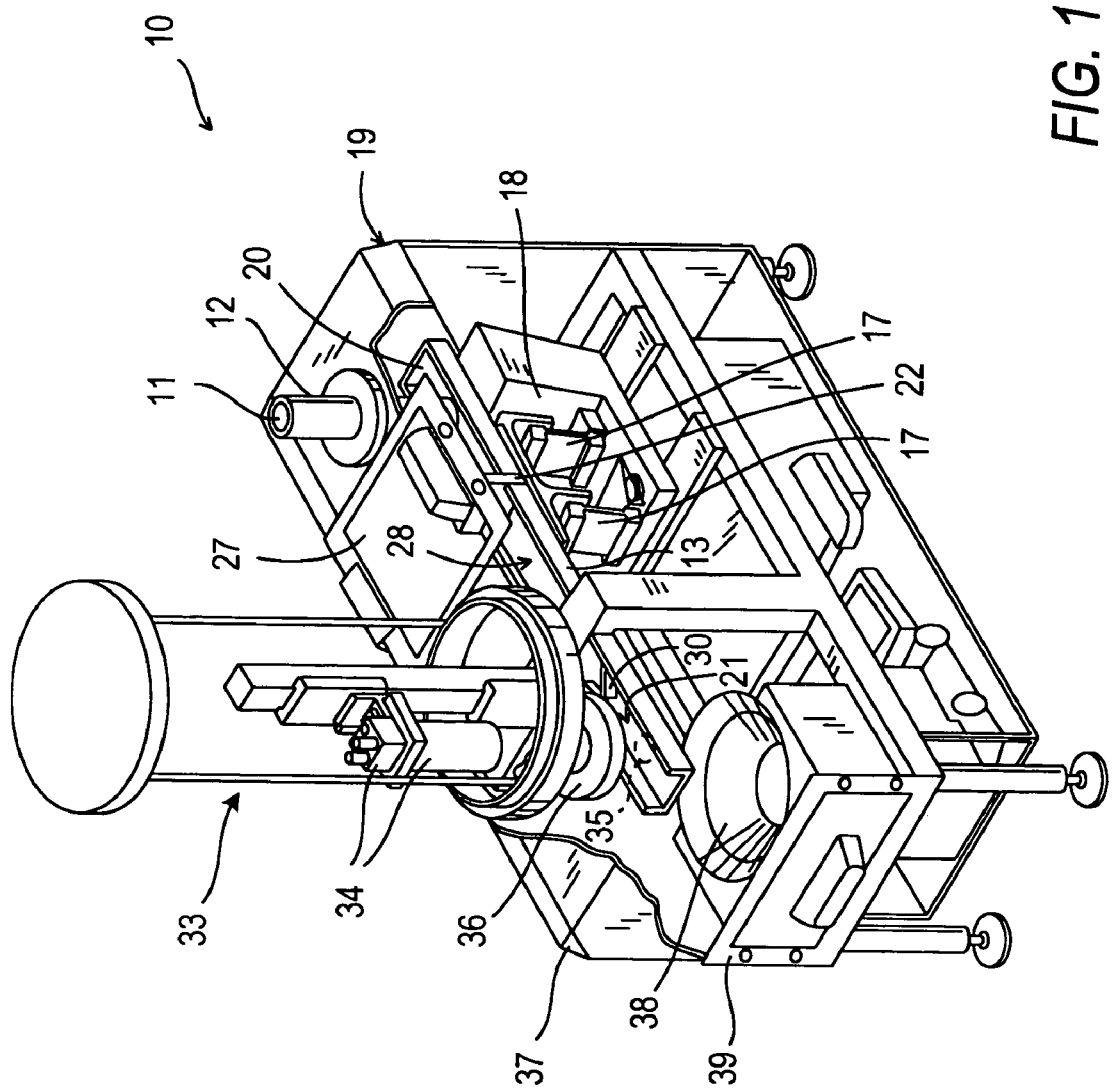
FIG. 1 shows a perspective view of one embodiment of an inspection device according to the present invention.
Figure 2:
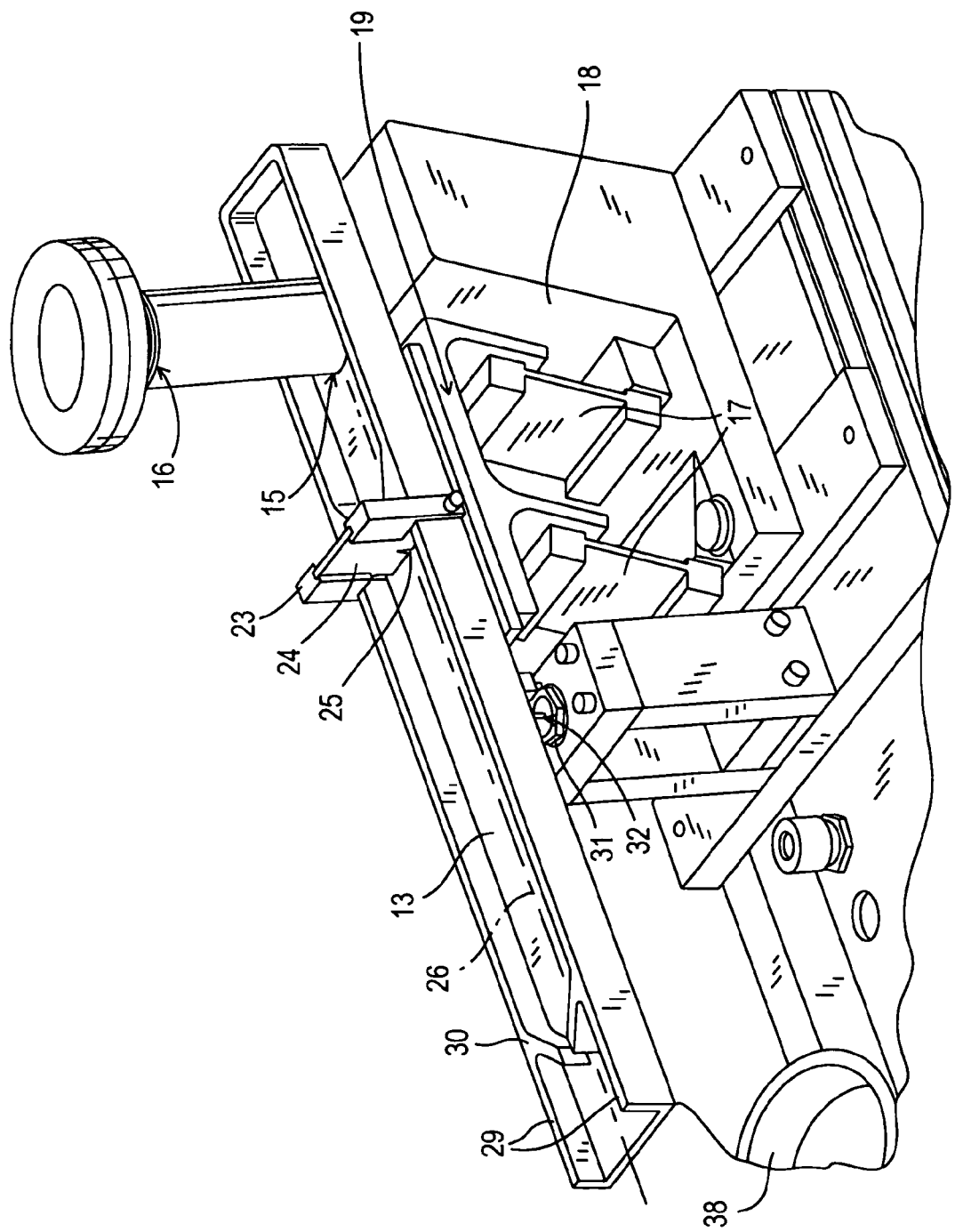
FIG. 2 shows a close-up view of a portion of the inspection device in FIG. 1.

FIGS. 1 and 2 show one embodiment of an inspection device 10 according to the present invention. A granular product may be poured into the entry spout 11 of the device, which guides the granular product through an entry shaft 12 to a receiving region 20 of an elongated feed tray 13, which is disposed substantially horizontally inside a housing 14 of the device 10. A gap 15 between an upper surface of the feed tray 13 and a lower end of the entry shaft allows the granular product to spread onto the feed tray 13. The size of the gap 15 may be adjustable (such as by rotating the entry shaft 12 on threads 16 so as to raise and lower the entry shaft with respect to the feed tray 13). Adjusting the gap 15 provides one way to control the amount of granular material which may move along the feed tray 13.

The feed tray 13, in this embodiment, is supported on its lower end by two struts 17 that extend upward from a vibrating device 18, which may include a vibrating motor inside of a motor housing. A bracket 19 may be interposed between the struts 17 and the feed tray 13 to form the connection.

When the vibrating device 18 is switched on, vibrations from the vibrating motor are imparted to the feed tray 13 through the struts 17 and bracket 19. Preferably, the elongated feed tray 13 vibrates back and forth in a longitudinal direction, or at least the movements include components in the longitudinal direction (i.e. in a direction parallel to the central axis 26) of the feed tray 13. In the embodiment shown in FIG. 1, the supporting struts 17 are both angled to the right. The vibrations imparted to the feed tray 13, cause a movement of the granules of the granular product on the feed tray in a general direction from the receiving region 20 to the imaging region 21 of the feed tray (i.e., in a right to left direction with respect to FIG. 1). The amplitude and frequency of the vibrating motor may be adjusted to increase or decrease the rate and other characteristics of the movement of the granules along the feed tray 13.

As the granules migrate from the receiving region 20 of the feed tray 13, they encounter a gate mechanism 22 disposed between the receiving region 20 of the feed tray and an intermediate region 28 of the feed tray. The gate mechanism includes gate posts 23 and a gate panel 24 having an orifice 25. The gate mechanism 22 allows only a controlled quantity of the granular product to pass through the orifice 25, while keeping the rest of the granular product in the receiving region 20. The gate posts 23 allow easy removal of the gate panel 24 and replacement with another gate panel having a different sized orifice or a different number of orifices. The gate panel orifice 25 shown in FIG. 1 is centered with respect to a width of the elongated feed tray 13, and thus has the additional effect of focusing the flow of granules toward the central axis 26 of the feed tray 13. An access door 27 is provided in the top of the housing to provide access to an operator of the inspection device, to change the gate panel 24 in the gate mechanism 22 or to otherwise access the components or product granules inside the inspection device 10.

After passing through the orifice 25 of the gate mechanism 22, the granules enter an intermediate region 28 of the feed tray. As the granules migrate through the intermediate region 28, the vibrations will tend to disperse the stream of granules out from the central axis 26 of the feed tray 13 and toward the side walls 29. Two deflectors 30, one protruding from each side wall of the feed tray, separate the intermediate region 28 from the imaging region 21 of the feed tray. The deflectors 30 focus the flow of granular product away from the walls 29 and toward the central axis 26 of the tray 13, as the granular product enters the imaging region 21 of the tray. Focusing the flow towards the central axis 26 reduces the amount of contact of the granular material with the side walls 29 in the imaging region 21 of the tray which may interfere with the flow and have undesirable effects on the image. Deflectors 30 may have various sizes and orientations relative to the wall of the tray as is optimal for providing product flow past the camera 34. Deflectors 30 may be adjustable (in size and/or orientation), or may be replaceable with deflectors of a different size and/or orientation. By controlling the flow with a fixed orifice 25 in gate mechanism 22, and fixed size and orientation of the deflectors 30, together with a fixed and repeatable vibration speed of vibrating device 18, the inspection device can image substantially the same amount of sample from analysis to analysis of the same substance which is important for obtaining meaningful and repeatable results for process control.

A tapping mechanism 31 is disposed underneath the intermediate region 28 of the feed tray 13. The tapping mechanism may include a solenoid or other known devices for activating a hammer element 32 for tapping the bottom surface of the feed tray. The tapping mechanism 31 may be disposed at other appropriate locations along the feed tray 13. The tapping mechanism can be activated to tap the feed tray 13 to dislodge one or more granules that may get stuck along the way from the receiving region to the imaging region or within either region. Granules may tend to stick to the floor or side walls 29 of the tray 13, or to the gate mechanism 22 or deflectors 30 due to the presence of static electricity, for example, or humidity or wetness of the granules or components.

A camera tower 33 is disposed on an upper side of the housing 14 which includes an image capturing device, which may be a camera 34. In general, a CCD imaging device can be used as the image capturing device. Other forms of detectors could also be used, including IR sensing devices and UV sensing devices, such as in cases in which chemical or temperature related wavelength emissions from the product can best be sensed by non visible detectors. In this embodiment, the camera 34 is disposed vertically with a lens pointing downwards toward an image area 35 of the imaging region 21 of the feed tray 13. The camera 34 may be connected to a microprocessor for performing image analysis on the images captured by the camera 34. A display device may also be provided for visual inspection of the granules by the device operator or other persons. The microprocessor preferably includes software for performing various analyses on the image, so as to determine characteristics of the granules being sampled, such as color and size characteristics of the granules, and to qualify and quantify characteristics of defects or foreign particles within the sample.

The same or a different microprocessor may be operationally connected to other components in the device such as the vibrating device 18, tapping mechanism 31, gate mechanism 22 and/or the illumination device 36, to provide user-friendly control options to these devices. Thus, the operator is preferably able to control the amplitude and/or frequency of the vibrating device 18 and the characteristics of the illumination of the sample, and to activate the tapping device 31, so as to provide optimal conditions for inspection of a particular sample depending on the granular product being inspected and the inspection characteristics being determined. The components are preferably controlled so as to facilitate replication of particular conditions for subsequent inspection operations.

The inspection device may include an illumination source, such as, in this embodiment, a ring light 36 that is disposed between the camera lens and the image area 35 on the tray 13. The ring light 36 is useful for providing light on all sides of the granules being imaged for improved imaging of the granules. A voltage regulator is preferably provided, in operational connection with the light source 36, so as to be able to control the intensity of light and to repeat particular lighting conditions in subsequent inspection operations. The color of the illumination provided by the light source may also be adjustable. A color of the tray 13, particularly a color of the tray surface within the image area 35, may be selected so as to provide good contrast with the defect and/or granules being imaged. For example, if the inspection device is being used to determine quantities of black speck within a sample, a color could be chosen that is close to the color of the normal product in the sample. If the inspection device is being used to determine particle size of the granular product, a color may be chosen to contrast with the color of the product. For a combined analysis of particle size and defect detection, the color may be chosen so as to provide contrast to both the good product particles and the defective ones.

After passing through the imaging region 21 of the tray, the granules reach the tray edge 37 and drop off into a catch bowl 38. A second access door 39 is provided in the inspection device 10 to remove the sampled product from the device. Alternatively, the inspection device 10 could be incorporated in-line to a production process for a granular product so that the granular product flows from an earlier production phase into the entry spout 12. Instead of the catch bowl 38, the granular product could move from the imaging region 22 of the tray 13 to a subsequent processing stage, such as by falling off the tray edge 37 into a funnel that is connected to the subsequent processing stage.

Figure 3:
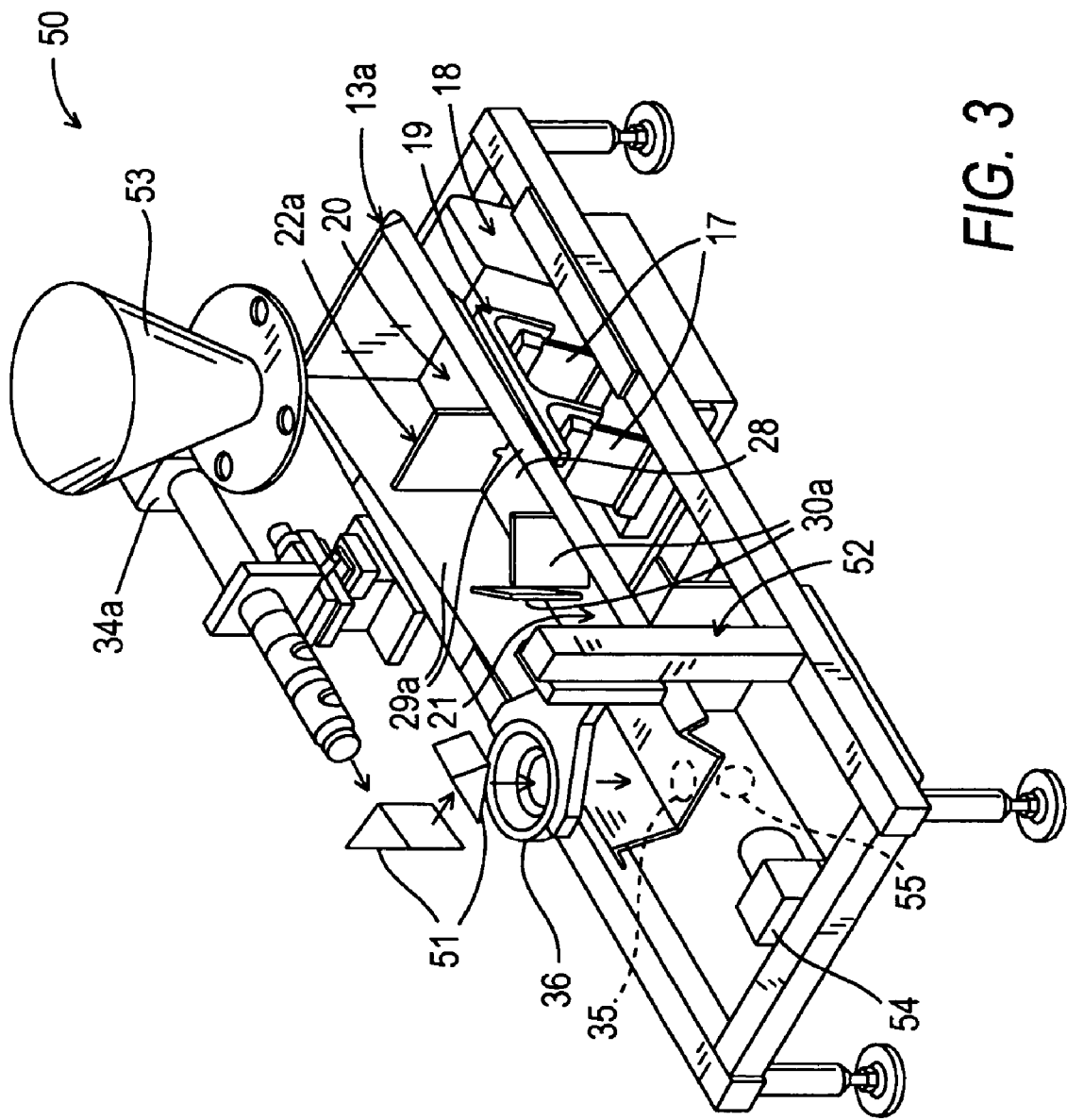
FIG. 3 shows a partial view of an alternative embodiment of an inspection device according to the present invention.

The alternative embodiment of the inspection device 50 shown in FIG. 3 offers a more compact design. Instead of being mounted vertically in a camera tower on top of the device, the image capturing device 34a in this embodiment is mounted horizontally within the housing (or, alternatively, on a side of the housing). Two prisms 51 are disposed to provide a view of the granules in the image area 35 to the image capturing device 34a. The feed tray 13a in shown in FIG. 3 includes higher side walls 29a which may be helpful for containing fine particles that become more easily airborne, and/or when using a high amplitude vibrations. Feed trays in this or other embodiments may have different shapes and sizes that may be used to suit the inspection requirements and the properties of the granular product being inspected. The ring light 35 is shown to be mounted to a post 52 and may be adjusted vertically for optimal illumination of a particular sample of granular product. The position of the lens of the camera 34a is, of course, also adjustable for optimizing the image. A funnel 53 is shown, which may be disposed over the entry spout in this or other embodiments to provide easier input of product into the entry spout.

A second image capturing device 54 may also be disposed on this or another embodiment so as to capture images of granules as they fall off of the edge of the feed tray through a second image area 55. The second image capturing device 54 may be used to obtain additional information about the granules such as size and shape information where product features and/or processing conditions are not optimal for extracting all information from the granules in the image area 35 of the feed tray. The second image capturing device 54 would preferably be accompanied by a second illumination source appropriately mounted so as to provide illumination of the particles in free fall. It may be connected to the same or a different microprocessor as the first image capturing device 34a for analysis of the image.

Figure 4:
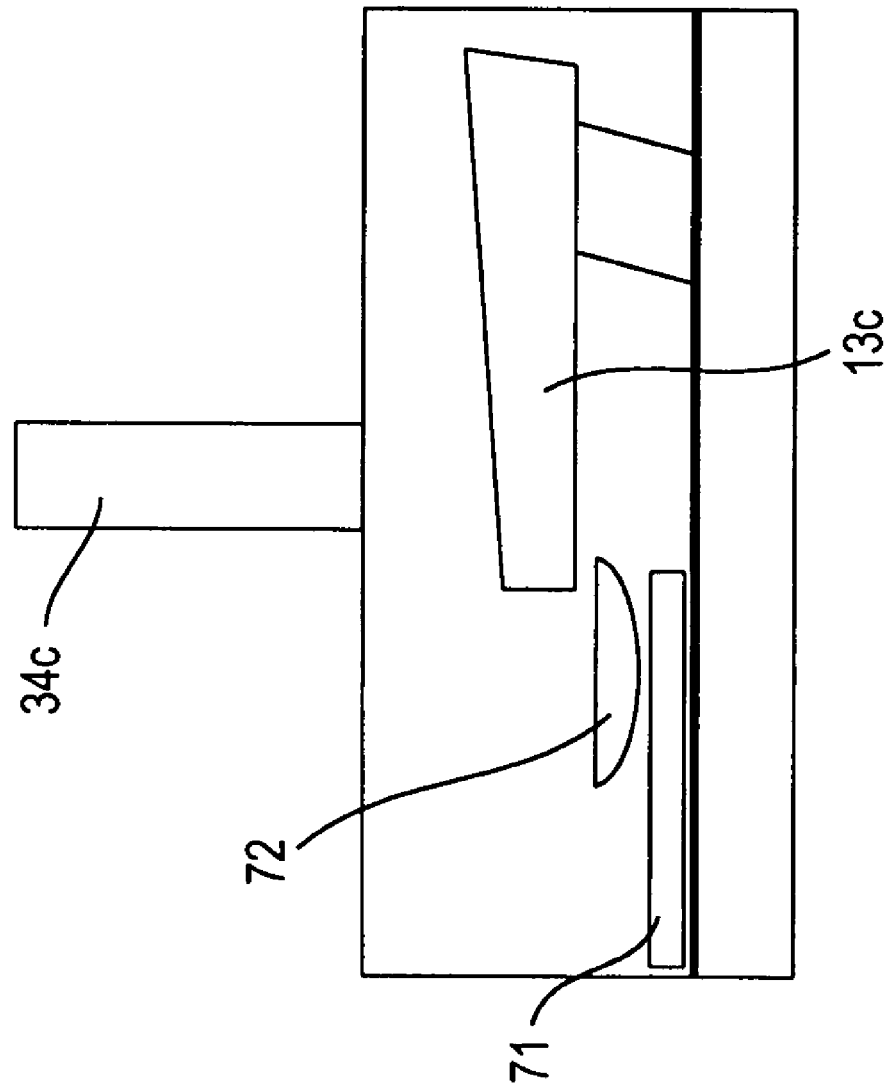
FIG. 4 shows a partial schematic representation of an inspection device according to the present invention having a scale.

FIG. 4 shows a schematic representation of an inspection device 70 including a scale 71 beneath the catch bowl 72. As the granules fall off the edge of the feed tray 13c into the catch bowl 72, the scale 71 detects the change in weight. Preferably, scale 71 is also connected to the same or a different microprocessor as the first image capturing device 34a or 34, so that the change in weight per unit time can be calculated and used together with the additional data being obtained by the inspection device. The detection of the change in weight is useful in many instances due to variations in the flow of the product. For example, when a dry particulate mixture in a container is emptied out through a chute or bottom opening in the container, there is a tendency for smaller particles to filter out first, leaving the last part of a batch with a greater percentage of larger particles. Given this tendency, the flow measured as weight per unit time will vary from the beginning of the batch to the end. Being able to inspect the granules per unit weight allows the operator to run a partial batch of a product and get meaningful results. This feature likewise accounts for variations in the speed of the flow which may be different at the start of the run than at the end.

In an advantageous embodiment, shown in FIG. 5, the inspection device may include a tray cover element 81, which covers the feed tray 13 so as to prevent airborne dust particles from the granular product from escaping the area of the feed tray. A chute element 82 may also be provided, which surrounds an area through which the particles fall from the edge 37 of the feed tray 13 into the catch bowl 38. Preferably, catch bowl cover 83 is also provided to keep airborne dust particles from escaping the catch bowl 38. Elements 81, 82, and 83 may be connected as a single element or may be separate elements that are operatively connected to one another. Particularly when inspecting a granular product that includes fine dust particles, it is advantageous to cover the entire path of the granular product from entry spout 11 to catch bowl 38. An excess of dust particles may cause undesired effects, such as, for example, harm to sensitive electronic components.

It will of course be understood that the present invention has been described above only by way of example and that modifications of details can be made within the scope of the invention.

What is claimed is:

1. An inspection device for inspecting a granular product, comprising:
   a feed tray having a receiving region for receiving the granular product and an imaging region;
   a vibration device confirmed to impart vibrations to the feed tray for moving granules of the granular product from the receiving region to the imaging region;
   a gate mechanism disposed upstream from the imaging area so as to control a flow of the granular product along the feed tray; and
   and an image capturing device configured to capture an image of a sample of the granular product in an image area of the imaging region of the feed tray.

2. The inspection device as recited in claim 1, wherein the feed tray has an elongate shape defining a central axis and first and second side walls.

3. The inspection device as recited in claim 2, further comprising a deflector element extending from the first and second side walls, the deflector element configured to focus a flow of the granular product toward the central axis.

4. The inspection device as recited in claim 2, wherein the vibrations include a component in a direction parallel to the central axis.

5. The inspection device as recited in claim 2, wherein the feed tray includes an edge disposed downstream from the image area, and further comprising a second image capturing device configured to capture an image of a second sample of the granular product falling off the edge of the feed tray through a second image area.

6. The inspection device as recited in claim 1, further comprising a tapping mechanism configured to tap the feed tray.

7. The inspection device as recited in claim 1, further comprising an entry spout in operable combination with the receiving region of the feed tray for supplying the granular product to the receiving region of the feed tray.

8. The inspection device as recited in claim 7, further comprising an entry structure between the entry spout and the receiving region of the feed tray, a gap being defined between the entry structure and a surface of the tray, wherein the gap is adjustable to control a flow of product onto the receiving region.

9. The inspection device as recited in claim 1, wherein the gate mechanism includes an orifice, a size of the orifice being adjustable.

10. The inspection device as recited in claim 9, wherein the orifice size is adjusted by substituting a first panel of the gate mechanism for a second panel of the gate mechanism.

11. The inspection device as recited in claim 1, wherein the image capturing device is disposed vertically above the image area.

12. The inspection device as recited in claim 1, further comprising at least one reflecting device for providing a view of the image area to the image capturing device.

13. The inspection device as recited in claim 1, further comprising an illumination source that includes a ring light, a view of the image area to the image capturing device passing through the ring light.

14. The inspection device as recited in claim 1, wherein at least one of an amplitude and a frequency of the vibrations is adjustable.

15. The inspection device as recited in claim 1, further comprising a catch bowl disposed downstream from the image area and a scale configured to detect a change in weight of the catch bowl.

16. The inspection device as recited in claim 1. further comprising a tray cover element covering at least a portion of the feed tray and configured to reduce an escape of dust from the feed tray.

17. The inspection device as recited in claim 16, further comprising a chute element at least partially disposed between the catch bowl and the image area and configured to reduce an escape of dust as the granular product moves from the image area to the catch bowl.

18. The inspection device as recited in claim 17, wherein the tray cover includes a translucent material.

19. The inspection device as recited in claim 18, wherein the chute element includes a translucent material.

20. A method for inspecting a granular product, the method comprising:
   disposing the granular product on a receiving region of a feed tray;
   vibrating the feed tray so as: to induce a movement of the granular product from the receiving region of the feed tray to an imaging region of the feed tray;
   controlling a flow of the granular product from the receiving region to the imaging region using a gate mechanism; and
   capturing an image of a sample of the granular product in an image area of the imaging region of the feed tray.

21. The method as recited in claim 20, further comprising adjusting a size of an orifice in the gate mechanism so as to adjust a flow rate of the granular product.

22. The method as recited in claim 20, wherein the feed tray has an elongated shape defining a central axis, and further comprising focusing a stream of the granular product toward the central axis of the feed tray using a deflector element.

23. The method as recited in claim 20, further comprising illuminating the image area using a ring light.

24. The method as recited in claim 20, further comprising analyzing the image using a microprocessor so as to determine a characteristic of the granular product.

25. The method as recited in claim 20, further comprising tapping the feed tray using a tapping mechanism.

26. The method as recited in claim 20, wherein the disposing of the granular product on the receiving region is performed using an entry structure defining a gap with a surface of the feed tray and further comprising adjusting the gap so as to control a flow rate of the granular product onto the receiving region.

27. The method as recited in claim 20, further comprising weighing the sample of the granular product using a scale.

28. The method as recited in claim 20, further comprising determining a change in weight of the sample per unit time.

29. The method as recited in claim 20, further comprising capturing a second image of the sample of the granular product during a free fall of the sample falls from an edge of the feed tray through a second image area.

* * * * *